United States Patent [19]

Teague, Jr. et al.

[11] 4,353,141

[45] Oct. 12, 1982

[54] POWER TOOTHBRUSH

[76] Inventors: W. Dorwin Teague, Jr., Tweed Blvd., Nyack, N.Y. 10960; Arthur T. Sempliner, 37-04 Van Nostrand Pl., Douglaston, N.Y. 11363

[21] Appl. No.: 166,705

[22] Filed: Jul. 7, 1980

Related U.S. Application Data

[60] Continuation-in-part of Ser. No. 920,685, Jun. 30, 1978, Pat. No. 4,210,975, which is a division of Ser. No. 848,807, Nov. 7, 1977, Pat. No. 4,175,299.

[51] Int. Cl.³ .............................................. A46B 13/06
[52] U.S. Cl. ..................................... 15/22 R; 128/47; 173/73; 173/169
[58] Field of Search .................. 15/22 R, 22 A, 22 C; 128/50, 66, 62 A, 47; 173/168, 169, 73; 51/170 MT

[56] References Cited

U.S. PATENT DOCUMENTS 3,878,577  4/1975  Jousson .............................. 15/22 R
4,146,020  3/1979  Moret ............................. 15/22 RX

*Primary Examiner*—Edward L. Roberts
*Attorney, Agent, or Firm*—Mandeville and Schweitzer

[57] ABSTRACT

The disclosure is directed to a water-powered toothbrush appliance or the like wherein the water-powered motor for driving the toothbrush is mounted in a hand held housing. A valve for controlling fluid flow to the water-powered motor is mounted in the housing and a valve control portion is rotatably mounted by the housing at an area thereof which generally underlies the thumb of a hand holding the appliance. The valve control portion is rotatable by the user's thumb to actuate the valve. In order to efficiently utilize the space within the housing, while maintaining optimum proportions thereof for convenient handling by the human hand, the valve is mounted within the housing on the side of the motor more distant from the valve control portion and the valve control portion is mechanically connected to the valve by an actuator which is arranged to pass directly through the nutating action motor.

10 Claims, 7 Drawing Figures

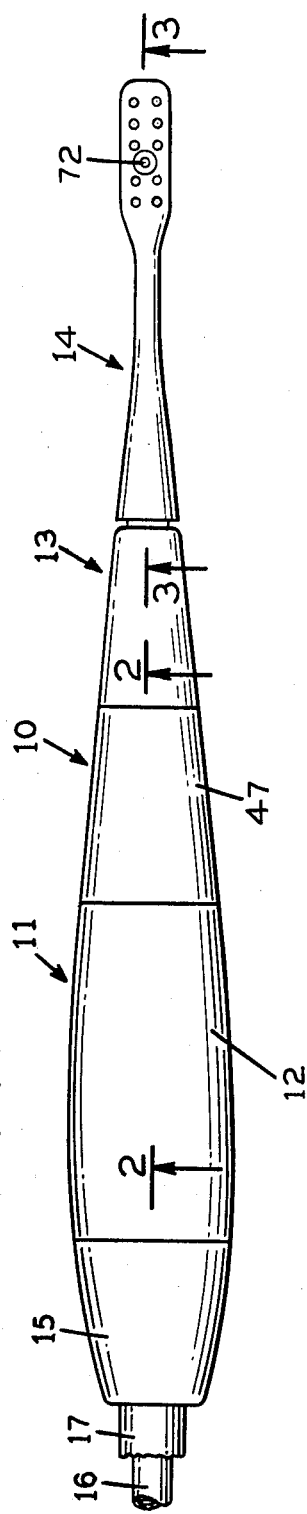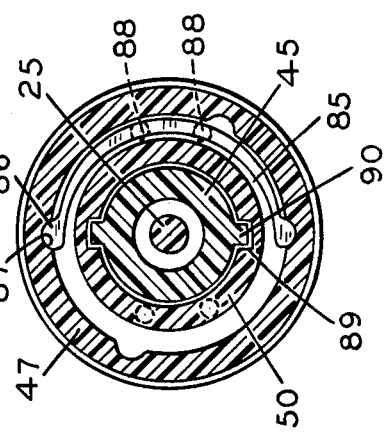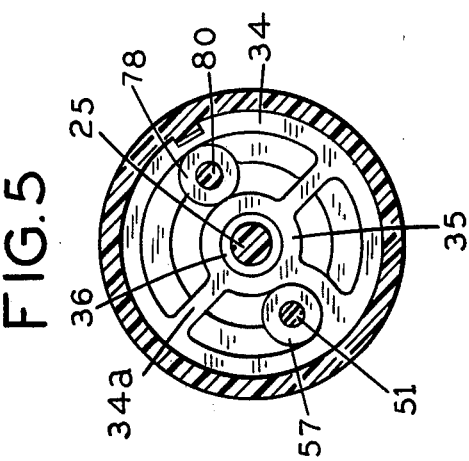

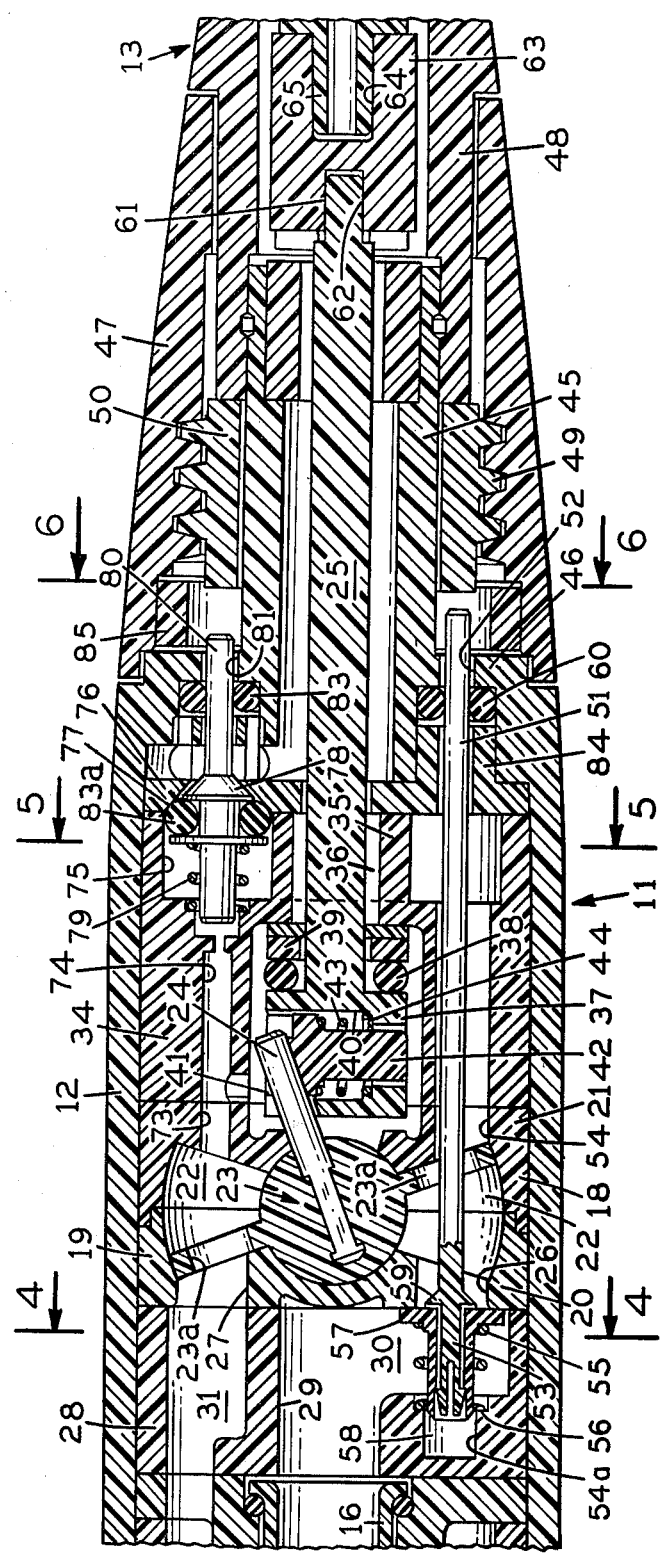

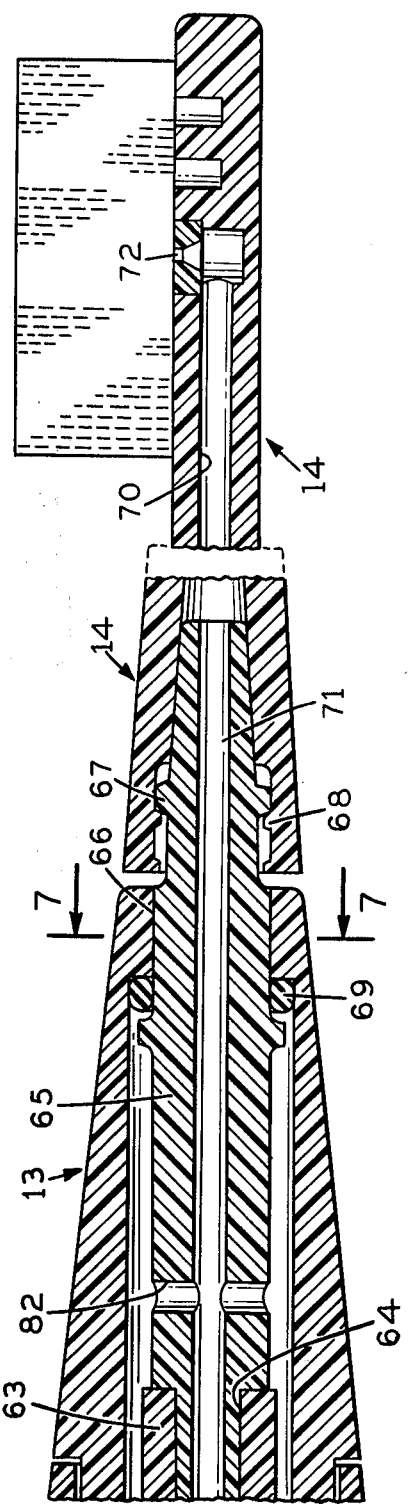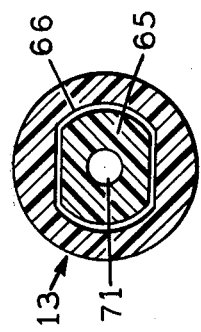

POWER TOOTHBRUSH

RELATED APPLICATIONS

The present application is a continuation-in-part of application Ser. No. 920,685, filed June 30, 1978, now U.S. Pat. No. 4,210,975, and is related in subject matter to application Ser. No. 070,689, filed Aug. 29, 1979, now U.S. Pat. No. 4,276,672, in turn a divisional application of application Ser. No. 848,807, filed Nov. 7, 1977, now U.S. Pat. No. 4,175,299.

BACKGROUND AND SUMMARY OF THE INVENTION

Power toothbrushes are well known and widely used home appliances. Generally, increased health consciousness has caused consumers to prefer the efficient and reliable mechanical brush action of such appliances to improve and maintain the good health of their teeth and gums. The working toothbrush element typically is driven through various rotary and/or linear reciprocating strokes for vigorous brushing and cleaning action which far exceeds the efficacy of inaccurate manual toothbrush manipulation. An example of a highly advantageous water-powered toothbrush appliance may be found in our co-pending application Ser. No. 070,689, filed Aug. 29, 1979.

In accordance with the disclosure of the co-pending application, motive power for the toothbrush element is provided by a water-powered, nutating action motor having an orbitally moving output member to drive the toothbrush element through an orbital motion without rotation. The primary working stroke of the brush over the teeth and/or gums is effectively largely unidirectional. During the return motion of the brush, its orbital path tends to retract it away from the teeth and gums, or at least lessen the pressure during the return stroke. This motion provides a brush stroke which approximates the theoretical ideal, in that the primary working stroke can be unidirectional, from the base of the gums, either upward or downward as the case may be, toward the tips of the teeth. Moreover, the device of the copending application is conveniently attachable to a household faucet as a source of driving fluid and affords safe, energy-efficient operation.

It is a primary objective of the present invention to provide an improvement in the basic design of nutating action, powered toothbrush appliances of the type disclosed in our copending application. In accordance with the invention, a unique arrangement of structural components is provided to reduce the overall length and width of the device for ease and comfort of handling by the user while affording reliable, convenient operation. Generally, the toothbrush comprises a handheld housing which mounts a nutating action, fluid-powered motor. The housing includes a valve control portion arranged in the portion of the housing proximate to the areas thereof engaged by a user's thumb when the device is held by a user for convenient manipulation thereof by the user. The valve-control portion is rotatable relative to the remainder of the housing and rotation thereof activates, through a novel mechanical arrangement, a valve-control rod to open and close the fluid source to the nutating action motor. In accordance with a significant feature of the invention, the valve-control rod is arranged to pass directly through the nutating motor itself to minimize the overall diameter of the handheld housing for easy handling of the toothbrush by the user.

The principle valve-control actuator is advantageously arranged for simple manipulation by the user in a manner which maintains the overall slim configuration of the appliance. In addition, the housing generally tapers gradually from the areas thereof held by the user's hand to the toothbrush. The valve-control portion is flush with the remaining portions of the housing and is positioned in the tapering areas of the housing to facilitate a natural gripping action by the user with the user's thumb lying on the valve-control portion. Moreover, as another feature of the invention, the valve-control portion of the housing may be rotated further after the valve has been opened to actuate a second valve mechanism whereby a portion of the motive fluid is diverted through the toothbrush appliance and out the bristles of the brush to provide a water-massage effect during brushing, if desired. To advantage, all of the various working and structural components of the device of the invention may comprise precision moldings of suitable structural plastic material joined together by adhesive or mechanical means, as deemed appropriate to the circumstances.

For a more complete understanding of the above and other features and advantages of the invention, reference should be made to the following detailed description of a preferred embodiment of the invention and to the accompanying drawings.

BRIEF DESCRIPTION OF THE DRAWINGS

FIG. 1 is a side view in elevation of a power toothbrush built in accordance with the principles of the present invention.

FIG. 2 is a partial side cross-sectional view of the power toothbrush taken generally along line 2—2 of FIG. 1.

FIG. 3 is a partial side cross-sectional view of the power toothbrush taken generally along line 3—3 of FIG. 1.

FIG. 4 is an end cross-sectional view of the power toothbrush taken generally along line 4—4 of FIG. 2.

FIG. 5 is an end cross-sectional view of the power toothbrush taken generally along line 5—5 of FIG. 2.

FIG. 6 is an end cross-sectional view of the power toothbrush taken generally along line 6—6 of FIG. 2.

FIG. 7 is an end cross-sectional view of the power toothbrush taken generally along line 7—7 of FIG. 3.

DETAILED DESCRIPTION OF A PREFERRED EMBODIMENT

Referring now to the drawings, and initially to FIGS. 1. and 2 thereof, there is illustrated a water-powered toothbrush built in accordance with the teachings of the present invention and generally indicated by the reference numeral 10. The power toothbrush 10 includes a main housing 11 comprising a central hand-grip portion 12 of relatively wide diameter which tapers gradually to a thin, front end portion 13. A removable toothbrush element 14 is mounted on the front end portion 13 for orbital, non-rotary motion, as will appear. The hand-grip portion 12 also tapers to an end cap member 15 which serves as an interconnect between the power toothbrush and a concentric tube arrangement 16, 17 for ingress and egress of a motive fluid such as, for example, water from a household faucet. To advantage, the concentric tube-fluid line connection may be of the type disclosed in out co-pending application Ser. No. 920,685 filed June 30, 1978, the disclosure of which is hereby expressly incorporated by reference. The fluid connection means of said co-pending application provides concentrically-arranged tubes with the pressure side of a household faucet connected to the innermost tube and the exhaust discharge side of the motor connected to the annular space between the inner and outer tubes. Moreover, the co-pending application teaches novel, simplified swivel connections between the appliance and the concentric tubes and also between the tubes and the outlet fitting of the faucet to permit rotation of the power toothbrush appliance relative to the concentric tube arrangement.

A nutating action motor 18 is mounted within the hollow interior of the hand-grip portion 12 of the main housing 11. The nutating action motor 18 includes a motor housing 19 comprising a lower housing section 20 and an upper housing section 21 which mate with one another to form an enclosed water chamber 22. In accordance with the known construction of nutating action motors, a saturn disc plate 23 is mounted with the water chamber 22 for universal tilting movement within predetermined limits. The saturn disc 23 rigidly mounts an output rod 24 which extends out of the nutating motor housing 19 and into the interior of the hand-grip portion 12 of the main housing 11.

As will be described in more detail hereinbelow, the output rod 24 is mechanically connected to a rotary drive member 25 in such a manner whereby the output rod 25 and saturn disc 23 are maintained at a predetermined, constant angularity with respect to the central axis of the motor housing 19. A dividing wall (not specifically illustrated) extends from the upper motor housing section 21 to the lower motor housing section 20 to divide the water chamber 22, as is well known in the nutating action motor art. Moreover, the lower motor housing section 20 is provided with a fluid input port 26 arranged on one side of the dividing wall and a fluid output port 27, arranged on the other side of the dividing wall.

In the operation of the nutating action motor, driving fluid will enter the input port 26 and flow around the water chamber 22 for discharge through the output port 27. As the driving fluid passes through the water chamber 22, it will continuously act against the tilted saturn disc 23 to move the saturn disc through progessively-changing tilt angles with respect to the central axis of the motor housing. The saturn disc 23 is provided with a plurality of port-like openings 23a whereby the driving fluid may pass below and above the saturn disc 23 during its passage through the water chamber 22. As a result of the progessively-changing tilt angle of the saturn disc 23, the output rod 24 is driven through a non-rotary orbital motion such that the outermost point thereof moves in a circular orbiting motion.

To interconnect the water chamber 22 with the concentric tubes 16, 17, a molded member 28 is received within the interior of the hand-grip section 12 of the main housing 11 below the motor housing 19. The molded member 28 is formed with a centrally disposed water conduit 29 which communicates via a transverse water chamber 30 with the input port 26 of the lower motor housing section 20. As most clearly illustrated in FIG. 4, the portions of the member 28 interior without the central conduit 29 and transverse water chamber 30 form a water discharge passage 31 which communicates directly with the water outlet port 27 of the nutating action motor 18. Several transverse members 32, 33 extend the full length of the member 28 to form a web separating the discharge passage 31 from the central conduit 29 and water chamber 30 and to provide structural strength for the member 28. To greatest advantage, the concentric tubes 16, 17 are rotatably connected to the central conduit 29 and discharge passage 31 respectively by means of the swivel fluid connectors disclosed in the aforementioned application Ser. No. 920,685. Accordingly, the toothbrush 10 may be easily connected to a household faucet as a source of motive fluid with the fluid discharge of the motor 18 returning to the sink associated with the faucet through the annular space between the concentric tubes 16, 17.

Arranged above the nutating action motor 18 is a second molded member 34 which is formed to include a cylindrical, sleeve-like portion 35 disposed along the central axis of the main housing 11 and supported within the member 34 by a plurality of web-forming elements 34a (see FIG. 5). The sleeve-like portion 35 mounts a rotor bushing 36, which in turn rotatably supports the rotary drive member 25. The rotary drive member 25 includes an offset shoe housing 37 integral with its lowermost end and an O-ring element 38 and washer bearing 39 are mounted concentric with the rotary drive member 25 between the shoe housing 37 and the rotor bushing 36 to retain the rotary drive member 25 from axial displacement. The shoe housing 37 defines a transverse bore 40 and includes an angularly-disposed slot opening 41, offset from the central axis of the motor housing 19, to receive the output rod 24 of the saturn disc 23, as illustrated. A shoe element 42 is slidably received within the bore 40 and is biased toward the output rod 24 by means of a coil spring 43 acting between an internal shoulder 44 formed within the bore 40 and the shoe element 42. The above-described arrangement provides a driving mechanical connection between the output rod 24 and the rotary drive member 25 with the coil spring 43, shoe element 42 configuration acting to maintain the output rod 24 in a canted position to provide the predetermined constant angularity of the saturn disc 23 for proper operation of the nutating action motor 18. To advantage, the output rod 24 may be displaced against the action of the spring 43 in the unlikely event that the nutating action motor 18 jams. This action will serve as a safety feature to protect the saturn disc 23 inasmuch as the displaceability of the output rod 24 against the shoe element 42 and spring 43 will permit the saturn disc 23 to straighten out under pressure from the motive fluid, whereby the motive fluid may pass directly through the water chamber 22 without causing any damage to the motor mechanism.

Referring now to FIG. 3 and the righthand side of FIG. 2, the forwardmost end of the rotary drive member 25 is formed to a flat extension of reduced width 61 which is received in a centrally-disposed, non-circular opening 62 formed in a mechanical connector 63. The connector 63 also includes an angularly-disposed, axially-offset opening 64. A hollow wobble shaft 65 is pivotally supported in a non-circular opening 66 formed through the forwardmost end of the housing section 13 (see FIG. 7) and includes a rear extension received in the angular, offset opening 64 of the mechanical connector 63. The orbital movement of the nutating motor output rod 24 will impart a rotary movement to the rotary drive member 25 via the mechanical connection between the output rod 24 and the shoe housing 37. Consequently, the rotary motion of the drive member 25 will rotate the mechanical connector 63 to drive the wobble shaft 65 in a pivoting, orbital motion about the pivot point defined by the non-circular opening 66 of the housing section 13. In this manner, the portions of the wobble shaft 65 extending outside the housing 11 will be driven through a non-rotary orbital motion. The wobble shaft is formed to include a circular, outwardly-extending rib 67 whereby a hollow end of the toothbrush 14 may be received over the end of the wobble shaft 65 such that the circular rib 67 passes beyond an inwardly-extending flange 68 formed within the interior of the hollow toothbrush 14 to mount the toothbrush 14 to the orbitally-movable wobble shaft 65. Accordingly, operation of the nutating action motor 18 will impart a highly advantageous orbital, non-rotating motion to the toothbrush 14. The orbital-to-rotary-to-orbital motion mechanical connection allows the orbital output of the nutating action motor 18 to be transmitted to the toothbrush 14 while minimizing the overall length of the housing 11.

To advantage, an O-ring seal 69 is mounted in a concentric relationship with the wobble shaft 65 on the internal side of the non-circular opening 66 to form a leak-tight seal. Moreover, the toothbrush 14 is provided with a fluid passage 70 integral with the hollow interior of the lowermost end of the toothbrush 14 and in fluid communication with the fluid passage 71 defined by the hollow wobble shaft 65. A portion of the motive fluid may be diverted from the discharge of the nutating action motor 18 through the passageways 71, 70 and out an opening or openings 72 arranged among the bristles of the toothbrush 14 to achieve a water-massage effect during brushing operations, if desired, as will be more fully discussed hereinbelow.

In accordance with the invention, a forward cylindrical extension 45 of reduced diameter is integrally connected to the hand-grip portion 12 of the main housing 11 by an inwardly extending, annular portion 46. A valve actuator portion 47 is received over the reduced-diameter forward extension 45 in a concentric, spaced relation thereto such that the exterior surface of the valve actuator portion 47 is flush with the exterior surface of the hand grip portion 12 of the main housing 11 and forms a gradually tapered continuation of the hand grip portion 12. The forwardmost section 13 of the housing 11 includes a skirt extension 48 which is received within the forwardmost open end of the valve actuator section 47 for a frictional engagement with the cylindrical extension 45, as clearly illustrated in FIG. 2. Referring once again to FIG. 1, it may be seen that the above-described configuration for the main housing 11, including the end cap 15, hand grip portion 12, valve actuator portion 47 and forward portion 13, provides a slim, gradually tapering housing for the toothbrush appliance 10 including a relatively wide diameter, hand grip portion 12 for easy gripping by the user with the user's thumb naturally engaging the valve actuator portion 47 for controlling the operation of the toothbrush appliance, as will be fully explained hereinbelow.

As clearly illustrated in FIG. 2, the valve actuator portion 47 is retained against axial displacement by the hand grip portion 12 of the main housing 11 on one side and by the tapered, forward portion 13 of the main housing 11 on the other side. Moreover, in the illustrated arrangement of the preferred embodiment, the valve actuator portion 47 is securely mounted to the housing 11 in a manner wherein the valve actuator portion 47 forms a section of the exterior surface of the toothbrush appliance 10 while being rotatable relative to the main housing 11.

In accordance with a significant feature of the invention, the valve actuator portion 47 is formed to include an internal thread 49 disposed along a predetermined portion of the interior surface of the rotatable valve actuator member 47. An internal nut 50 is threadedly engaged with the internal thread 49 of the actuator portion 47 and is in a concentric relationship with the reduced diameter, forward extension 45 and rotary drive member 25. Referring now more particularly to FIG. 6, the internal nut 50 is provided with two diametrically opposed, axially extending grooves 89 which mate with complementary axial ribs 90 formed along the outer surface of the forward cylindrical extension 45 whereby the internal nut 50 is prevented from rotation. Accordingly, as the valve actuator portion 47 is rotated by a user of the toothbrush appliance 10, the interaction of the internal thread 49 thereof with the non-rotatable internal nut 50 will cause the internal nut 50 to move axially with respect to the housing 11, either toward or away from the nutating action motor 18, depending on whether the valve actuator portion 47 is rotated in a clockwise or counterclockwise direction.

A valve actuator rod 51 extends from a point directly below the internal nut 50 through an opening 52 formed in the annular member 46, and the housing section 12 to a mechanical connection with a valve plug 53 seated upon and normally closing the fluid input port 26 of the motor housing 19. Pursuant to the teachings of the invention, the valve actuator rod 51 is received through an opening 54 formed in the upper motor housing section 21 and passes directly through the motor housing 19 and one of the ports 28 of the saturn disc 23 whereby the rod 51 is co-axial with the input port 26 and aligns with and connects to the valve plug 53. This novel arrangement for the valve actuator rod 51 provides significant advantages in that the rod 51 is ideally positioned for valve actuation from an area of the housing 11 forward of the nutating action motor 18 and proximate the thumb of the user permitting convenient manipulation. At the same time, by passing the rod 51 directly through the motor housing 19 and saturn disc 23, the rod 51 aligns with the valve plug 53 while minimizing the overall diameter needed to accommodate the working components of the toothbrush device 10 within the hand grip section 12. In a practical embodiment of the invention, the outer diameter of the section 12 may be in the order of 0.984 inches which is adequate to mount a nutating action motor suitable to drive a toothbrush while being an ideal dimension for holding and handling the device by a human hand.

To advantage, the valve plug 53 is arranged within the water chamber 30 of the molded member 28 and aligned with a recess 54a formed in the water chamber 30 and capable of receiving the valve plug 53 when the rod 51 acts to displace the plug 53 from its normally closed position over the fluid input port 26. A coil spring 55 acts between an annular shoulder 56 formed at the outer end of the recess 54 and a flange 57 formed at the lowermost portion of the valve plug 53 to urge the plug 53 toward its normally closed position. The plug 53 itself is formed to a hollow, tube-like member including a portion 58 of expanded inner diameter. The actuator rod 51 includes a resilient, tapered fork end which is received within the plug 53 until the fork end expands within the expanded inner portion 58 and seats against the shoulder dividing the portion 58 from the remaining interior portions of the valve plug 53. An outwardly flaring, cone-shaped portion 59 is integral with the rod 51 and serves to hold the valve plug 53 against the tapered fork end of the rod 51. To advantage, an O-ring seal 60 is mounted around the rod 51 near the opening 52 to prevent any of the motive fluid from leaking therethrough.

In the operation of the device, the user rotates the valve actuator portion 47 until the internal nut 50 engages and displaces the rod 51 against the action of the spring 55 to open the input port 26. The motive fluid is then free to flow into the water chamber 22 of the motor 18 to drive the toothbrush, as described above. The angle of the helix of the internal thread 49 is formed to achieve an optimum degree of rotation for the valve actuator portion 47 in going from the off condition to the on condition of the toothbrush and vice versa. To assist the operator, a horseshoe-shaped central spring 85 is mounted within the valve actuator portion 47 by a frictional engagement between bulb-shaped protruberances 86 formed at the ends of the spring 85 and semicircular cut-outs 87 in the valve actuator portion 47. The spring 85 includes two rod-like extensions 88 which engage the internal nut 50 to indicate to the operator that the valve actuator portion 47 has been rotated a sufficient amount for toothbrush actuation.

Pursuant to another feature of the invention, the upper motor housing section 21 is provided with a fluid opening 73 arranged opposite the fluid discharge port 27 whereby a portion of the motive fluid discharge from the motor may flow out the port 73 into a fluid passage 74 formed within the molded member 34. The passage 74 expands to a fluid chamber 75 which is in fluid communication with the annular space between the rotary drive member 25 and the interior of the forward extension 45 of the hand grip section 12 of the housing 11. A circular disc 76 is received within the hand grip section 12 such that a portion thereof is in a confronting relation with the fluid chamber 75. The confronting portion includes a tapered valve seat 77 and a valve plug 78 disposed within the fluid chamber 75 is biased to a normally closed position with the valve seat 77 by a coil spring 79. The valve plug 78 is provided with an integral rod-like extension 80 which extends through an opening 81 formed in the annular portion 46 to a position directly below the internal nut 50.

In accordance with the invention, the forwardmost end of the rod-like extension 80 is disposed below the forwardmost end of the valve actuator rod 51 whereby the internal nut 50 must be displaced beyond the valve actuation position to engage and displace the rod-like extension 80. Continued rotation of the valve actuator section 47 after the toothbrush has been activated will cause a displacement of the valve plug 78 away from the valve seat 77 whereby a portion of the motive fluid will flow through the valve seat 77 and into the annular space between the rotary drive member 25 and the extension 45. Referring now to FIG. 3, transverse bores 82 are formed through the wobble shaft 65 to provide fluid communication from the valve seat 77 to the internal fluid passage 71 of the wobble shaft 65. Thus, the valve actuator section 45 may be used to both turn the toothbrush on and off and to activate the water-massage feature of the invention.

To advantage, an O-ring seal 83a may be placed around the valve plug 78 to assure a leak-tight seal when the plug 78 is seated in the valve seat 77. An O-ring seal 83 is mounted around the rod-like extension 80 to prevent fluid from leaking through the opening 81 of the annular portion 46. In addition, the circular member 76 is formed to include an integral cylindrical bushing 84 to support and guide the valve actuator rod 51 during axial movement thereof.

The present invention provides a hand held, fluid-powered appliance comprising a highly advantageous arrangement of structural and working components to achieve a highly effective working action while allowing the appliance housing to be ideally proportioned for convenient handling, manipulation and operation by one hand of a user. The slim-line, gradually tapering configuration for the housing affords a natural gripping action by the user's hand with the user's thumb overlying the valve actuator portion so that it may be easily rotated relative to the housing in either direction to open and close fluid flow to the appliance. Moreover, the inventive concept of arranging the valve actuator rod within the nutating action motor itself with the rod passing through a port-like opening formed in the saturn disc provides a reliable, effective and efficient mechanical means for a valve actuation to open and close the nutating action motor, while minimizing the housing diameter. Thus, the housing may be formed to an optimum diameter for handling by the user with ample space to mount a nutating action motor. The overall configuration for the appliance housing and valve actuator portion, as taught by the present invention, provides the art with a significant improvement in hand held appliance design.

It should be understood, of course, that the specific form of the invention herein illustrated and described is intended to be representative only, as certain changes may be made therein by those skilled in the art without departing from the clear teachings of the disclosure. Accordingly, reference should be made to the following appended claims in determining the full scope of the invention.

We claim:

1. A water-powered appliance comprising
   (a) a housing,
   (b) a working element movably associated with one end of said housing,
   (c) orbital output drive means within said housing for driving said working element through a predetermined motion,
   (d) said orbital output drive means comprising a fluid-powered, nutating motor having a motor housing,
   (e) a saturn disc mounted within said motor housing for universal tilting movement within predetermined limits,
   (f) a source of motive fluid for driving said saturn disc through said tilting movement,
   (g) said appliance housing being of a size and shape to be held by one hand of an operator with the thumb of the holding hand extending generally toward the forward end of the housing associated with said working element and on one side of said nutating action motor,
   (h) a valve operating member mounted by said appliance housing for rotational movement relative to said housing and being mounted in the area of said housing engaged by the thumb of the holding hand,
   (i) said valve-operating member being rotatable by thumb motion of the operator,
   (j) a valve providing fluid communication between said source of motive fluid and said nutating motor, (k) said valve being mounted within the housing on the side of the motor opposite the thumb engaging portion of the appliance housing, and (l) a rod-like valve actuator extending within said appliance housing from the valve-operating member to the valve and passing directly through the saturn disc of the nutating action motor, (m) said rod-like valve actuator being axially movable by rotation of said valve-operating member to actuate said valve.

2. The water-powered appliance according to claim 1, further characterized by (a) said saturn disc including a port-like opening formed therethrough, (b) said rod-like valve actuator extending through said port-like opening.

3. The appliance according to claim 1, further characterized by (a) said valve-operating member comprising a hollow, sleeve-like element rotatably mounted on said appliance housing, (b) said sleeve-like element including an internal thread portion, (c) a nut element non-rotatably mounted within the housing and threadedly engaging the threaded portion of said sleeve-like element, (d) whereby rotation of said sleeve-like element causes an axial displacement of the non-rotatable nut, (e) one end of said rod-like valve actuator being disposed directly below said nut and being movable by the axial displacement of said nut to operate said valve.

4. The appliance according to claim 3, further characterized by (a) said motor housing including an inlet port, (b) said valve comprising a normally closed, spring-biased valve plug being in a leak-tight sealing relation with said inlet port, (c) said rod-like valve actuator being connected to said valve plug and operable upon being displaced by said nut to move said spring-biased valve plug away from the inlet port whereby motive fluid from said source of motive fluid may enter the motor housing to drive said saturn disc.

5. The water-powered appliance according to claim 3, further characterized by (a) means forming a fluid flow path from said motor housing to said working element, (b) a second valve mounted between said motor housing and said means forming a fluid flow path, (c) said rotatable valve-operating member being operable upon rotation thereof to open said second valve.

6. The appliance according to claim 5, further characterized by (a) said second valve including an integral actuator element with one end thereof being disposed directly below said nut element and being spaced below the outermost end of said rod-like valve actuator whereby upon rotation of said sleeve-like, valve-operating member said nut element will be displaced to first engage and move said rod-like valve element and then engage and operate said second valve after said rod-like valve actuator has been displaced sufficiently to open said inlet port of the nutating motor to fluid flow.

7. The water-powered appliance according to claim 3, further characterized by (a) said working element comprising a toothbrush and including a wobble shaft pivotally mounted in said appliance housing, (b) said output drive means including an output rod rigidly mounted to said saturn disc and movable thereby through an orbital motion during the tilting movement of the saturn disc, (c) one end of said wobble shaft being mechanically connected to said output rod whereby the orbital motion of said output rod is transmitted to the wobble shaft thereby driving said toothbrush through a non-rotary, orbital motion.

8. A water-powered appliance comprising a housing, (b) a working element movably associated with one end of the housing, (c) a nutating action motor mounted within the housing and being disposed toward the end of the housing opposite said end associated with the working element, (d) said nutating action motor including a saturn disc mounted for universal tilting movement within predetermined limits, (e) a source of motive fluid for driving said saturn disc through progressively-changing tilt angles, (f) said nutating action motor being mechanically connected to said working element, (g) a valve-operating member rotatably supported by said housing near the end thereof associated with said working element, (h) a valve interconnecting said source of motive fluid and said nutating action motor and being disposed within said housing near said opposite end, (i) a valve actuator mechanically associated with said valve-operating member and extending from said valve-operating member to said valve directly through the saturn disc of the nutating action motor.

9. The water-powered appliance according to claim 8, further characterized by (a) said appliance housing including a hand grip section being of a size and shape to be held by one hand of an operator, (b) said valve-operating member comprising a hollow, sleeve-like element rotatably mounted on said appliance housing between said hand grip section and the end of the appliance housing associated with said working element whereby the thumb of the holding hand generally overlies said sleeve-like, valve-operating member.

10. The water-powered appliance according to claim 9, further characterized by (a) said sleeve-like, valve-operating member being flush with and generally forming a gradually tapering extension of the hand grip section of the appliance housing.

* * * * *